(12) United States Patent
Kishimoto et al.

(10) Patent No.: US 7,927,625 B2
(45) Date of Patent: Apr. 19, 2011

(54) SUGAR-COATED AGENT

(75) Inventors: Junichi Kishimoto, Tokyo (JP); Reiko Tanaka, Tokyo (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 267 days.

(21) Appl. No.: 11/885,971

(22) PCT Filed: Mar. 9, 2006

(86) PCT No.: PCT/JP2006/304611
§ 371 (c)(1),
(2), (4) Date: Nov. 8, 2007

(87) PCT Pub. No.: WO2006/095819
PCT Pub. Date: Sep. 14, 2006

(65) Prior Publication Data
US 2008/0193533 A1 Aug. 14, 2008

(30) Foreign Application Priority Data
Mar. 10, 2005 (JP) ................................ 2005-066476

(51) Int. Cl.
*A61K 9/24* (2006.01)
*A61K 9/36* (2006.01)
(52) U.S. Cl. ........ 424/472; 424/479; 424/480; 427/2.21
(58) Field of Classification Search .................. None
See application file for complete search history.

(56) References Cited

U.S. PATENT DOCUMENTS

| 4,312,893 A | | 1/1982 | Futter | |
|---|---|---|---|---|
| 5,098,715 A | * | 3/1992 | McCabe et al. | 424/479 |
| 6,709,676 B2 | * | 3/2004 | Cho | 424/472 |

FOREIGN PATENT DOCUMENTS

| EP | 1 391 201 A1 | | 2/2004 |
|---|---|---|---|
| JP | 47-3995 A | | 2/1972 |
| JP | 50-124715 A | | 10/1975 |
| JP | 56-87518 A | | 7/1981 |
| JP | 57-134414 A | | 8/1982 |
| JP | 63-93713 A | | 4/1988 |
| JP | 1-230513 A | | 9/1989 |
| JP | 2-138117 A | | 5/1990 |
| JP | 5-33685 A | | 5/1993 |
| JP | 8016052 | * | 2/1996 |
| JP | 09-143055 | * | 6/1997 |
| JP | 9-143055 A | | 6/1997 |
| JP | 09143055 | * | 6/1997 |
| JP | 2002-179559 A | | 6/2002 |
| JP | 2004-99543 A | | 4/2004 |

OTHER PUBLICATIONS

JP 09-143055 Machine Translation as provided by http://dossier1.ipdl.inpit.go.jp/AIPN/odse_top_dn.ipdl?N0000=7400.*
FLS, Inc. translation of JP 09143055 above—translated Sep. 2009.*
Ohmori et al, 2004 (International Journal of Pharmaceutics, vol. 278:459-469.*
JP 08016052 (as noted above) Machine translation.*
Extended European Search Report dated Aug. 26, 2010.

* cited by examiner

*Primary Examiner* — Blaine Lankford, Jr.
*Assistant Examiner* — Raymond P Yeager
(74) *Attorney, Agent, or Firm* — Sughrue Mion, PLLC

(57) ABSTRACT

A sugar-coated agent that includes a core, a film layer that mainly includes a film component, the outer surface of the core being coated with the film layer, a sugar coating layer that mainly includes a sugar coating component, the outside of the film layer being coated with the sugar coating layer, and a middle layer that includes a film component and a sugar coating component and is provided between the film layer and the sugar coating layer, wherein within the middle layer, the concentration of the sugar coating component at the interface between the middle layer and the sugar coating layer is higher than the concentration of the sugar coating component at the interface between the middle layer and the film layer.

12 Claims, 7 Drawing Sheets

SUGAR-COATED AGENT

TECHNICAL FIELD

The present invention relates to a sugar-coated agent.

RELATED ART

A sugar-coated tablet is a dosage form in which an uncoated tablet is coated with a several layers of sugar. A sugar-coated agent such as the sugar-coated tablet has an attractive appearance, is easily taken, can mask odor, bitterness, and unpleasant appearance, and can guarantee drug stability. Because of this, it is widely preferred as a general dosage form. In particular, it is suitable as the dosage form for a drug or a supplement or the like that is taken every day and contains a component such as vitamin or an amino acid having poor stability.

In a conventional production process for a sugar-coated tablet, an uncoated tablet is coated with a sugar coating syrup using a sugar coating pan or a coating apparatus. The sugar-coated tablet thus obtained has on the outside of the uncoated tablet several layers, including a layer for rounding the tablet, a layer for imparting strength, and a layer for making the surface attractive or the like. In this case, since the syrup is fully spread over an edge part of the uncoated tablet, the sugar coating part is 70% to 100% of the uncoated tablet weight. Because of this, the tablet becomes large, and there is room for improvement in terms of ease of taking.

Furthermore, since an interface is formed between layers forming the sugar-coated agent, the strength becomes poor in some cases. In particular, in a thin layer sugar-coated tablet in which the thickness of the sugar coating layer is reduced, this lack of strength is noticeable. Because of this, cracks, chips, et cetera, might be caused due to impact, and when provided as a product, it is necessary to carry out a complicated procedure such as putting a cushioning material such as padding into a container.

Moreover, when coating using a sugar coating pan, since the operation is a skilled one, variations in the quality of preparations obtained easily occur due to the technique of workers.

Since a sugar-coated agent is a dosage form having excellent properties, it is widely used at present, and wide-ranging investigations into the automation of coating processes and techniques of thin layer sugar coating are being carried out. On the other hand, with regard to the sugar coating techniques, there is room for improvement in terms of the above-mentioned points.

As conventional techniques related to sugar-coated agents, there are those described in patent Documents 1 to 5.

Patent Document 1 discloses a technique in which talc is added to a sugar solution, and coating is carried out by a continuous spray method so that the sugar coating layer weight is 9% to 40% of the uncoated tablet weight. In accordance with the method described in this publication, a thin layer sugar-coated tablet that is free from problems such as cracking is believed to be obtained.

Furthermore, Patent Document 2 discloses a technique of making a thin layer by adding a water-soluble cellulose derivative and a low-substituted hydroxypropyl cellulose as binders so as to increase the strength of a sugar coating layer.

Moreover, Patent Document 3 discloses a technique of making a thin layer of a sugar coating layer by continuously spraying an erythritol solution.

Furthermore, Patent Documents 4 and 5 disclose a technique of increasing the strength of a tablet by additionally providing between layers a cushioning layer to which a sugar and an additive are added.

On the other hand, as tablets, film tablets are generally widely used. Since the film tablet has a thin coated layer, it is suitable for making a small tablet and has the advantage that it is resistant to cracking, et cetera, but there are the defects that when taken it has an unpleasant taste characteristic of a film and, furthermore, since moisture, et cetera, permeates, the component content mixed in the tablet decreases.

Furthermore, the above-mentioned Patent Document 5 discloses a technique related to a sugar-coated tablet having an inner core on which a film coating has been applied. In this publication, there is described a sugar-coated tablet having, between the film layer of the inner core and a sugar coating layer, a middle layer formed from a water-soluble macromolecule and a water-soluble sugar.

Patent Document 1: Japanese laid-open patent publication No. S56-87518

Patent Document 2: Japanese examined patent publication No. H5-33685

Patent Document 3: Japanese laid-open patent publication No. 2002-179559

Patent Document 4: Japanese laid-open patent publication H9-143055

Patent Document 5: Japanese laid-open patent publication 2004-099543

DISCLOSURE OF THE INVENTION

However, the above-mentioned conventional techniques each have room for improvement in terms of the following.

Firstly, a large amount of talc is present on the surface of a tablet obtained by the method described in Patent Document 1. Because of this, there is a possibility that barrier properties toward moisture or oxygen might become insufficient. Furthermore, since there is a taste of talc when taken, there is room for improvement in terms of ease of taking.

Furthermore, in the case of sugar-coated tablets obtained by the methods described in Patent Document 2 and Patent Document 3, sufficient strength cannot be guaranteed in some cases.

Moreover, although the techniques described in Patent Document 4 and Patent Document 5 are effective to some extent as methods of preventing peeling between layers with respect to Patent Document 2 and Patent Document 3, the techniques have room for further improvement in terms of impact strength.

Specifically, when the present inventors examined the existing thin layer sugar coating techniques, it was clear that a sugar-coated tablet having a middle layer between a film layer of an inner core and a sugar coating layer of an outer core has higher impact strength than a sugar-coated tablet having no middle layer. It is surmised that the reason that the impact strength becomes high is because providing the middle layer containing a film component and a sugar coating component between the film layer and the sugar coating layer enables adhesion at the interfaces between the middle layer and the film layer and sugar coating layer to be improved, thus improving the impact strength to some extent compared with a constitution in which no middle layer is provided.

However, even in the case where a middle layer is provided, crack can be caused by impact in some cases, and there is room for further improvement in the impact resistance.

It is an object of the present invention to provide a sugar-coated agent having a higher impact strength than that of the conventional techniques.

According to the present invention, there is provided a sugar-coated agent that includes a core, a film layer that mainly includes a film component, the outer surface of the core being coated with the film layer, a sugar coating layer that mainly includes a sugar coating component, the outside of the film layer being coated with the sugar coating layer, and a middle layer that includes a film component and a sugar coating component, the middle layer being provided between the film layer and the sugar coating layer, wherein within the middle layer the concentration of the sugar coating component at the interface between the middle layer and the sugar coating layer is higher than the concentration of the sugar coating component at the interface between the middle layer and the film layer.

As hereinbefore described, the middle layer provided in the conventional sugar-coated agent is provided from the viewpoint of improving adhesion between the film layer and the sugar coating layer by adding components of both the film layer and the sugar coating layer. Because of this, the sugar coating component composition within the middle layer is uniform, the difference in concentration of the sugar coating component at the interface of the film layer and the middle layer and at the interface of the middle layer and the sugar coating layer is still large, and there is a possibility that peeling, et cetera, might occur at the interface. Furthermore, in the conventional constitution, the difference in concentration of the sugar coating component between the film layer and the sugar coating layer is merely shared by the interfaces between the middle layer and the two layers as a result of increasing the number of interfaces by providing the middle layer. Because of this, there was no concept of providing a component distribution in the middle layer.

In contrast to this, in the present invention, by providing a distribution in concentration of the sugar coating component in the middle layer, it is possible to reinforce an area of low impact strength that is present in the coated layer even in the case of a middle layer being provided, that is, the interface. By providing the middle layer, the number of interfaces from the film layer to the sugar coating layer increases. In particular, it is surmised that the interface between the film layer, in which the sugar coating component concentration is substantially zero, and the middle layer, in which it is not zero, is an area that, among the coated layers, has particularly low impact strength. This also applies to the interface between the middle layer and the sugar coating layer. In the present invention, by making the constitution such that the sugar coating component concentration in the middle layer at the interface between the film layer and the middle layer is lower than the sugar coating component concentration in the middle layer at the interface between the middle layer and the sugar coating layer, these interfaces are reinforced. This enables the impact resistance of the coated layers to be improved.

According to the present invention, there is provided a coating apparatus that coats the surface of a core, the apparatus including a first supply unit supplying a first liquid, a second supply unit supplying a second liquid, a mixing unit mixing the first liquid and the second liquid, a spraying unit spraying a mixed liquid mixed by the mixing unit onto the surface of the core, and a control unit constituted so as to spray the mixed liquid onto the core while changing the mixing ratio of the first liquid and the second liquid in the mixed liquid.

Furthermore, according to the present invention, there is provided a process for producing the above-mentioned sugar-coated agent of the present invention, the process including forming the middle layer by spraying a mixed liquid of a first liquid containing a film component and a second liquid containing a sugar coating component onto the core while changing the mixing ratio of the first liquid and the second liquid in the mixed liquid.

According to the present invention, since the mixed liquid can be sprayed onto the core while changing the mixing ratio of the film component and the sugar coating component in the mixed liquid, it is possible to stably produce a middle layer in which the concentration of the sugar coating component changes along the lamination direction.

In addition, any combination of these constitutions, and those achieved by converting between methods, equipment, et cetera, of the expressions of the present invention are also effective as modes for carrying out the present invention.

For example, according to the present invention, there is provided a sugar-coated agent wherein, with regard to a solid preparation including a core coated with a coated layer, the coated layer includes as components a film component and a sugar coating component, the coated layer having a portion that is closest to the core coated with a coating agent including the film component alone or mainly including the film component, the proportion of the sugar coating component gradually increasing as it goes further from the core, and the outermost layer having a coated layer that is coated with a coating agent including the sugar coating component alone or mainly including the sugar coating component.

According to the present invention, there is provided a drug coating apparatus that includes a sprayer employing at least two liquid feed pumps, that is, a liquid feed pump that feeds a liquid including a film component and a liquid feed pump that feeds a liquid including a sugar coating component.

Furthermore, according to the present invention, there is provided a process for producing the above-mentioned sugar-coated agent of the present invention, the process including forming a coating layer having a concentration gradient from the inside to the outside by a sprayer employing at least two liquid feed pumps, that is, a liquid feed pump that feeds a liquid including a film component and a liquid feed pump that feeds a liquid including a sugar coating component while continuously changing the flow rate of each of the liquid feed pumps.

As hereinbefore described, in accordance with the present invention, since the interfaces can be reinforced by a constitution in which the concentration of the sugar coating component at the interface between the middle layer and the sugar coating layer is made higher than the concentration of the sugar coating component at the interface between the middle layer and the film layer, the impact resistance of the sugar-coated agent can be improved.

BRIEF DESCRIPTION OF THE DRAWINGS

The above and other objects, features and advantages of the present invention will be more apparent from the following preferred embodiments taken in conjunction with the accompanying drawings, in which.

BEST MODE FOR CARRYING OUT THE INVENTION

Figure 1:
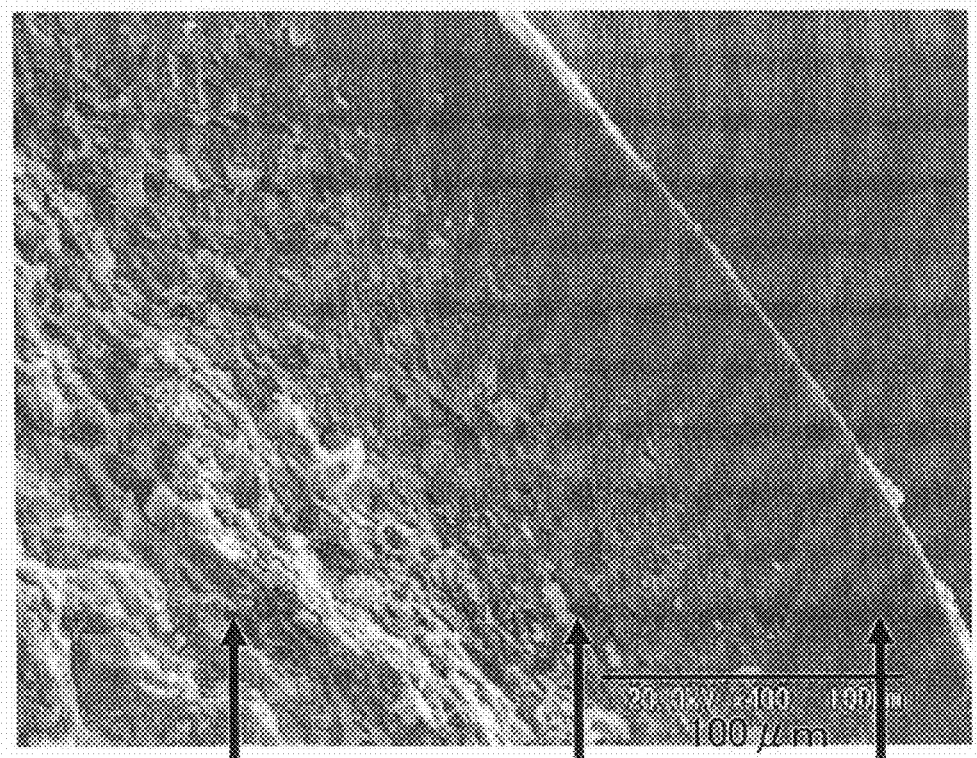
FIG. 1 A diagram showing an electron microscopic image of a cross section of a sugar-coated tablet of an Example, FIG. 2 A diagram showing an electron microscopic image of a cross section of a sugar-coated tablet of a Comparative Example, FIG. 3 A diagram showing the result of detecting methanethiol in tablets of Examples, FIG. 4 A diagram showing the result of an odor sensory test for tablets of Examples, FIG. 5 A diagram showing the result of a vitamin B1 stability test for tablets of Examples, FIG. 6 A diagram showing the result of a moisture absorption test for tablets of Examples, and FIG. 7 A diagram showing the result of a test of ease of taking tablets of Examples.

The sugar-coated agent of the present invention is a sugar-coated preparation formed from a core and a coated layer with which the outer surface of the core is coated. The sugar-coated agent of the present invention may be, for example, a sugar-coated tablet or granule.

The core referred to in the present invention is a coating target that can be orally ingested such as a coating target containing a principal drug component; a tablet is preferable in terms of ease of operation or the like, but it is also possible to coat a particulate such as a granule. When a tablet is used as the core, in addition to a tablet generally called an uncoated tablet, naked tablet, or the like, it is also possible to coat a tablet that has been coated with such as a film component having high affinity for a coating agent of the present invention that is to be applied to an area that is closest to the core.

Furthermore, it is possible to add to the core of the present invention an appropriate drug and a generally used component that is used for the production of a normal tablet such as an excipient, a lubricant, a disintegrant, or the like.

The coated layer includes a film layer with which the outer surface of a core is coated, a sugar coating layer with which the outside of the film layer is coated, and a middle layer provided between the film layer and the sugar coating layer.

The constitution of each layer is specifically explained below.

The film layer is formed mainly from a film component. The sugar coating layer is formed mainly from a sugar coating component.

In the present invention, 'formed mainly from a film component' and 'formed mainly from a sugar coating component' means that of the components remaining after drying the majority is the film component or the sugar coating component respectively, and includes those containing another component at a level that does not impair the effect of the present invention. Specifically, it means that of the components remaining after drying approximately 90 mass % or more is the film component or the sugar coating component.

In the present invention, since the film layer is mainly formed from a film component, it is possible to suppress the penetration of moisture into the core.

In the present invention, the amount of coating with a layer formed only from the film component or a layer formed mainly from the film component, which protects the core from the penetration of moisture by virtue of the film component, depends on the size of the core, for example, core particles, but it is usually preferably 0.1 to 30 mass % relative to the mass of the core, and more preferably at least 5 mass % from the viewpoint of protecting the core from moisture penetration during coating.

In the present invention, as the film component, a macromolecule used in a general film coating tablet may be used. Furthermore, when a sugar-coated agent is produced by mixing the film component with a sugar coating component and spraying on a core, it is necessary to use a water-soluble macromolecule that has good compatibility with the sugar coating component. Specific examples thereof include hydroxypropyl methyl cellulose, gum arabic, polyvinyl pyrrolidone, polyvinyl alcohol, pullulan, or the like, and they may be used singly or in a combination of two or more types.

With regard to macromolecules used as the film component, some thereof exist as various different types according to the specification, and since they are different in terms of compatibility with the sugar coating component, et cetera, it is preferable to use the film components as a mixture. The compatibility may be confirmed experimentally simply by mixing an aqueous solution of the film component and an aqueous solution of the sugar coating component and checking the transparency.

For example, as hydroxypropyl methyl cellulose, hydroxypropyl methyl cellulose 2910 as specified by the Pharmacopeia of Japan, such as TC-5R manufactured by Shin-Etsu Chemical Co., Ltd.; and hydroxypropyl methyl cellulose 2208 as specified by the Pharmacopeia of Japan, such as SB-4 manufactured by Shin-Etsu Chemical Co., Ltd.; et cetera. can be used. Moreover, the film component may be a mixture of hydroxypropyl methyl cellulose 2910 and hydroxypropyl methyl cellulose 2208.

Furthermore, it is possible to add to the film component an aggregation inhibitor such as talc or magnesium stearate;

a plasticizer such as triethyl citrate, triacetin, or polyethylene glycol;

a colorant such as titanium oxide; and a disintegrant such as calcium carmellose or a low-substituted hydroxypropyl cellulose; et cetera.

The sugar coating layer is now explained.

The sugar coating layer is a layer formed only from the sugar coating component or mainly from the sugar coating component. The proportion of the sugar coating component in the sugar coating layer is on the order of an amount that can form a sugar coating layer. On the order of the amount, it is preferable that can form a sugar coating region as a layer on the entire outer surface of the middle layer.

Furthermore, the sugar coating layer may be the outermost layer of the sugar-coated agent. In this case, the proportion of the sugar coating component in the layer formed only from the sugar coating component or mainly from the sugar coating component is preferably an amount that can coat the entire surface.

As the sugar coating component, one or more materials selected from the group consisting of sucrose, erythritol, mannitol, sorbitol, xylitol, maltitol, and reduced lactose may be used. Furthermore, from the viewpoint of operability the sugar coating component used in the present invention is preferably a water-soluble sugar having a solubility in water at 25° C. of 0.3 to 3 g/g. Examples of such a sugar include maltitol, erythritol, glucose, sucrose, and the like. Among these, sucrose is the most preferable since water in the coating liquid can be further reduced and a drying step can be shortened.

In the present invention, in order for the tablet surface to appear attractive, it may be given a syrup coating.

The middle layer is now explained.

In the middle layer, the concentration of the sugar coating component in the middle layer at the interface between the middle layer and the sugar coating layer is higher than the concentration of the sugar coating component in the middle layer at the interface between the middle layer and the film layer. In this constitution, a discontinuous plane may or may not be present in the sugar coating component composition across the region from the interface between the film layer and the middle layer to the interface between the middle layer and the sugar coating layer. In the case of a constitution in which there is no discontinuity (discontinuous face) in the sugar coating component composition, the impact resistance of the coated layer can be further improved.

Furthermore, the middle layer may be a layer in which the mixing ratio of the sugar coating component is gradually varied. The layer in which the mixing ratio is gradually varied in the present invention is such that the concentration is steplessly varied from a mixing ratio at which the film component dominates to a mixing ratio at which the sugar coating component dominates or is varied stepwise to a degree such that no interface is produced between layers.

On the other hand, the concentration of the film component in the middle layer may be varied gradually according to the concentration distribution of the sugar coating component. It is also possible to provide a component distribution for the film component in the same manner as for the sugar coating component. Specifically, the concentration of the film component at the interface with the film layer may be higher than the concentration of the film component at the interface between the middle layer and the sugar coating layer. By so doing, the impact resistance of the sugar-coated agent can be further improved.

Furthermore, the middle layer may contain a third component other than the film component and the sugar coating component. Moreover, the third component may be a material that improves the compatibility between the film component and the sugar coating component. By adding such a component, the strength of the interior of the middle layer and the entire coated layer can be yet further improved.

Specific constitutions of the middle layer are as follows.
(i) A constitution in which the middle layer includes a gradient layer in which the concentration of the sugar coating component increases continuously from the film layer side to the sugar coating layer side, and
(ii) a constitution in which within the middle layer the concentration of the sugar coating component increases stepwise from the film layer side to the sugar coating layer side.

Each thereof is explained in further detail below.
(i) Constitution in which the Middle Layer Includes a Gradient Layer in which the Concentration of the Sugar Coating Component Increases Continuously from the Film Layer Side to the Sugar Coating Layer Side In this constitution, the gradient layer is a layer having a stepless concentration gradient of the sugar coating component, and has substantially no discontinuity in the concentration of the sugar coating component. Because of this, a constitution can be provided in which a stress concentration point is not present in the interior of the gradient layer. Because of this, the impact resistance of the sugar-coated tablet can reliably be improved.

Furthermore, in the constitution in which a gradient layer is provided, the middle layer may be formed from one or more gradient layers. This enables the generation of a stress concentration point in the middle layer to be more reliably suppressed.

Moreover, in this constitution, the concentrations of the sugar coating component at the interfaces of a plurality of gradient layers may match each other.

Furthermore, the constitution may be such that, at the interface between the middle layer and the sugar coating layer, the type and the concentration of the sugar coating component in the middle layer are the same as the type and the concentration of the sugar coating component in the sugar coating layer. By so doing, since the constitution may be such that the interface between the middle layer and the sugar coating layer does not coincide with a discontinuity in the sugar coating component composition, it is possible to further enhance the strength of the interface between the middle layer and the sugar coating layer.

Moreover, the constitution may be such that the coated layers from the film layer to the sugar coating layer do not have a discontinuity in composition at which the sugar coating component composition changes discontinuously. The sugar coating component composition referred to here means the type and the concentration of the sugar coating component. By so doing, for a constitution in which it is necessary to employ several layers of coating for making a thin layer and there are interfaces between the layers, it is possible to further improve the impact resistance of the sugar-coated agent.

In addition, the concentration of the film component may also, in the same manner as for the sugar coating component, be decreased continuously in the gradient layer from the film layer side to the sugar coating layer side. By so doing, since a discontinuity in concentration is not formed in the gradient layer for the film component either, it is possible to yet further improve the impact resistance of the sugar-coated agent.

Furthermore, the constitution may be such that, at the interface between the film layer and the middle layer, the type and the concentration of the film component in the film layer are the same as the type and the concentration of the film component in the middle layer. By so doing, since the constitution may be such that the interface between the film layer and the middle layer does not coincide with a discontinuity in the film component composition, it is possible to further improve the strength of the interface between the film layer and the middle layer.

Moreover, according to the constitution in which there is no discontinuity in composition, at which the film component composition would change discontinuously, in going from the film layer to the sugar coating layer, the impact resistance of the sugar-coated agent can be yet further improved. The film component composition referred to here means the type and the concentration of the film component.

Furthermore, the constitution may be such that the gradient layer has substantially no interface. In the sugar-coated agent of the present invention, the core is adjacent to the film layer or a layer formed mainly from the film component, and since the concentration ratio of the film layer to the sugar coating layer gradually changes toward the outside, it is possible to form a thin layer sugar-coated tablet having a coating layer with no interface. By gradually changing the mixing ratio steplessly from the film layer, which is the innermost layer, to the sugar coating layer, which is the outermost layer, to thus eliminate the interface, it is possible to provide a sugar-coated preparation that has stronger impact resistance and enables the coated layer to be made thinner while maintaining a good appearance and good ease of taking, which are advantages of a sugar-coated tablet.

In the gradient layer in which the concentration ratio of the film component and the sugar coating component is gradually changed, with regard to the proportion of each component, although it depends on the size of the core, the water-soluble macromolecule is usually preferably 0.1 to 50 mass % relative to the mass of the core, and the proportion of the sugar coating component is usually preferably 0.1 to 200 mass % relative to the mass of the core, although it depends on the size of the core. In the gradient layer of the present invention, the mixing ratio is changed from one in which the film component is dominant to one in which the sugar coating component is dominant so that the final mixing proportions fall in the above-mentioned ranges. Here, from the viewpoint of improvement in the ease of taking the proportion of the sugar coating component in the gradient layer is preferably not less than 100 mass % relative to the water-soluble macromolecule, and more preferably not less than 150 mass %.

Furthermore, for example, when TC-5R (product name: hydroxypropyl methyl cellulose 2910) is used as the film component and sucrose is used as the sugar coating component, since the compatibility therebetween is poor, when the sugar coating proportion becomes high, continuous coating becomes impossible, but by adding SB-4 (product name: hydroxypropyl methyl cellulose 2208) to the film component, continuous coating becomes possible. The mixing ratio of TC-5R and SB-4 is preferably in the range of 3:1 to 1:1. When the proportion of SB-4 is too low, the compatibility between the film component and sucrose is degraded, and when the proportion of SB-4 is too high, the tablet strength deteriorates.

(ii) Constitution in which within the Middle Layer the Concentration of the Sugar Coating Component Increases Stepwise from the Film Layer Side to the Sugar Coating Layer Side In this constitution, the concentration of the sugar coating component changes stepwise within the middle layer. Furthermore, the middle layer is formed from two or more layers having different sugar coating component concentrations.

When the middle layer has the above constitution, since the difference in concentration of the sugar coating component at the interface between the film layer and the middle layer and the difference in concentration of the sugar coating component at the interface between the middle layer and the sugar coating layer can be made small, it is possible to improve the strength of the interface in the same manner as in the above-mentioned (i). Furthermore, by making the constitution such that the middle layer includes three or more layers having different sugar coating component concentrations, the impact resistance of the sugar-coated agent can be further improved.

Moreover, in the middle layer having the above constitution, the constitution may be such that the concentration of the film component is decreased stepwise from the film layer side to the sugar coating layer side. This enables the impact strength of the sugar-coated agent to be yet further improved.

Since the sugar-coated agent of the present invention has the middle layer as above, it is possible to eliminate the defects of the conventional sugar-coated agent while maintaining excellent points such as ease of taking and appearance.

That is, in accordance with the present invention, a thin layer sugar-coated tablet having excellent ease of taking and high strength can be obtained.

Furthermore, by making sugar crystals on the surface of the tablet compact, it is possible to impart a barrier capability (humidity, oxygen), which is a characteristic of the sugar-coated tablet. Specifically, in order to avoid an increase in the size of the sugar coating layer, when it is made into a thin layer, compared with the case the amount of macromolecule being increased so as to introduce strength, it is possible to avoid an increase in the permeability of the coating. Because of this, it is possible to suppress any deterioration in the masking of odor, change in appearance, and the barrier capability toward moisture or oxygen, et cetera. The sugar-coated agent of the present invention is therefore arranged so as to exhibit an excellent effect in stabilizing the components therein. It is therefore possible to fully obtain the unpleasant odor masking effect, which is a characteristic of the sugar-coated tablet, and the effect of stabilizing a drug as a result of low gas permeability, low moisture permeability, et cetera.

It is therefore possible to utilize the sugar-coated agent of the present invention in pharmaceuticals, quasi drugs, food for specific health uses, health foods, food, et cetera.

Furthermore, the sugar-coated agent of the present invention may include a flavoring. By adding a flavoring, it is possible to form a preparation having excellent ease of taking. Moreover, it has been found that the stability of a flavoring component is superior compared with a case where it is added to a film tablet of a Comparative Example. With regard to the flavoring used here, normal flavorings in general may be used.

A process for producing the sugar-coated agent of the present invention is now explained.

The sugar-coated agent of the present invention is obtained by coating the surface of a core with a coated layer. In this process, a middle layer may be formed by spraying a mixed liquid of a first liquid containing a film component and a second liquid containing a sugar coating component in the mixed liquid onto the core while changing the mixing ratio of the first liquid and the second liquid.

Furthermore, when forming the coated layer, as a coating apparatus, one may be used that includes a first supply unit supplying the first liquid, a second supply unit supplying the second liquid, a mixing unit mixing the first liquid and the second liquid, a spraying unit spraying a mixed liquid mixed by the mixing unit onto the surface of the core, and a control unit having a constitution such that the mixed liquid is sprayed onto the core while changing the mixing ratio of the first liquid and the second liquid in the mixed liquid. The first supply unit supplies the first liquid containing, for example, the film component, and the second supply unit supplies the second liquid containing, for example, the sugar coating component. In this process, the control unit sprays the mixed liquid onto the core while changing the ratio of the film component and the sugar coating component in the mixed liquid.

Furthermore, as the coating apparatus, one having a sprayer employing at least two liquid feed pumps, that is, a liquid feed pump feeding a liquid containing the film component and a liquid feed pump feeding a liquid containing the sugar coating component may be used.

A more specific explanation is made below with, as an example, a case of the constitution (i) above in which the middle layer includes a gradient layer in which the concentration of the sugar coating component increases continuously from the film layer side to the sugar coating layer side.

When forming the gradient layer, by continuously changing the flow rate of each liquid feed pump of the sprayer employing at least two liquid feed pumps, that is, the liquid feed pump feeding the liquid containing the film component and the liquid feed pump feeding the liquid containing the sugar coating component, a coating layer having a concentration gradient from the inside to the outside can be formed. The film layer, the middle layer, and the sugar coating layer may also be formed by a continuous process.

More specifically, a core such as an uncoated tablet or a granule obtained by a standard production method is subjected to coating by use of a sprayer that can feed a coating liquid formed from the film component and a coating liquid formed from a sugar by one pump or two or more pumps, and spray the two solutions as a mixture when spraying, while imparting a concentration gradient (gradient) such that there is a gradual change from a coating liquid formed only from the film component or mainly from the film component to a coating liquid having a high sugar concentration, and it is thus possible to coat the core steplessly without introducing an interface. In this process, it is more preferable from the viewpoint of mixture uniformity to mix each of the solutions with a mixer partway along a pipe and then feed them.

Since the sugar-coated preparation of the present invention can be produced by a combination of two pumps, a pump controller, and a normal film coating apparatus, it is possible to produce it by simply modifying conventional equipment.

It is also possible to obtain the sugar-coated agent of the present invention in a simple manner without modifying equipment by a method in which coating liquids whose mixing ratio has been adjusted stepwise in advance are sprayed using only one pump, or a method in which the film component is charged into a pump intake portion, liquid feeding is started, and the sugar coating component is then gradually added to the pump intake portion.

As a result of an investigation by the present inventors, the strength of the tablet can be guaranteed by preparing a coating layer without an interface by imparting a concentration gradient from the macromolecule layer adjacent to the core to the sugar coating layer, which is the outermost layer. Furthermore, a barrier function toward moisture, oxygen, et cetera, can be expected because the outermost layer is mainly formed from a sugar, and a tablet which gives a sweet taste when taken, thus having excellent ease of taking, can be obtained.

Since it is also possible to spray continuously using a normal coating apparatus, the production cost can be suppressed and, furthermore, the amount of coating can be reduced. Because of this, it becomes possible to provide a small sugar-coated tablet that is easily taken.

The present invention includes the following modes.

(1) A sugar-coated agent wherein, with regard to a solid preparation that includes a core coated with a coated layer, the coated layer includes as components a film component and a sugar coating component, the coated layer having a portion that is closest to the core coated with a coating agent including the film component alone or mainly including the film component, the proportion of the sugar coating component gradually increasing as it goes further from the core, and the outermost layer having a coated layer that is coated with a coating agent including the sugar coating component alone or mainly including the sugar coating component.

(2) The sugar-coated agent according to (1), wherein the film component is one or more materials selected from the group consisting of hydroxypropyl methyl cellulose, gum arabic, polyvinyl pyrrolidone, polyvinyl alcohol, and pullulan.

(3) The sugar-coated agent according to (1), wherein as the film component hydroxypropyl methyl cellulose 2910 and hydroxypropyl methyl cellulose 2208 are used, and as the sugar coating component sucrose is used.

(4) The sugar-coated agent according to (1), wherein the sugar coating component is one or more selected from the group consisting of sucrose, erythritol, mannitol, sorbitol, xylitol, maltitol, and reduced lactose.

(5) The sugar-coated agent according to (1), wherein the sugar-coated agent is a sugar-coated tablet.

(6) The sugar-coated agent according to (1) wherein the sugar coating solution further contains a flavoring component.

(7) A drug coating apparatus that includes a sprayer employing at least two liquid feed pumps, that is, a liquid feed pump that feeds a liquid including a film component and a liquid feed pump that feeds a liquid including a sugar coating component.

(8) A process for producing the sugar-coated agent according to (1), the process including forming a coating layer having a concentration gradient from the inside to the outside by a sprayer employing at least two liquid feed pumps, that is, a liquid feed pump that feeds a liquid including a film component and a liquid feed pump that feeds a liquid including a sugar coating component while continuously changing the flow rate of each of the liquid feed pumps.

(9) The process according to (8), wherein each of the liquids are mixed with a mixer partway along a pipe and supplied.

EXAMPLES

The present invention is explained in further detail by reference to Examples, Comparative Examples, and Test Examples.

Example 1

Production of Uncoated Tablet 2055 g of lactose for direct tableting, 600 g of crystalline cellulose, 300 g of low-substituted hydroxypropyl cellulose, and 30 g of vitamin B1-nitrate were mixed in a mixer, 15 g of magnesium stearate was further added thereto and mixed, and the mixture was then subjected to tableting using a rotary tableting machine to give uncoated tablets with a weight of 300 mg (9 mm diameter) per tablet.

[Coating with Film Layer]

152 g of hydroxypropyl methyl cellulose 2910 (TC-5R, manufactured by Shin-Etsu Chemical Co., Ltd.), 39 g of hydroxypropyl methyl cellulose 2208 (SB-4, manufactured by Shin-Etsu Chemical Co., Ltd.), 50 g of talc, and 1.8 L of purified water were well stirred to give a macromolecule solution.

2500 uncoated tablets were charged into an aeration type coating apparatus (DRC-300, manufactured by Powrex Corp.), and coated up to 5% (15 mg) of the uncoated tablet weight by spraying at 4 g/min.

[Middle Layer Coating (Gradient Layer)]

167 g of sugar and 1.5 L of purified water were stirred well to give a sugar solution. A thin layer sugar-coated tablet was obtained by continuously spraying, by means of a Dria coater 300 (DRC-300, Powrex Corp.), the macromolecule solution used for film layer coating and the sugar solution using two pumps while changing the mixing ratio of the solutions so that the proportion of the sugar solution gradually increased, and the final proportion of the sugar solution was 100%. The amount of coating per tablet was 85 mg (of which the gradient layer was 70 mg).

Example 2

Uncoated tablets and a film layer were obtained in the same manner as in Example 1. Subsequently, a middle layer was formed from a plurality of layers having different sugar coating component concentrations.

[Middle Layer Coating (Multistep)]

6 parts of the macromolecule solution and 4 parts of the sugar solution of Example 1, which had been prepared in advance, were continuously sprayed using the Dria coater at a coating amount of 20 mg per tablet. Subsequently, 2 parts of the macromolecule solution and 8 parts of the sugar solution were prepared and then continuously sprayed using the Dria coater at a coating amount of 20 mg per tablet. Finally, a sugar syrup was prepared from 70 g of sugar and 30 mL of purified water, and sugar coating was carried out to give a coating amount of 10 mg per tablet using a sugar coating pan to give thin layer sugar-coated tablets.

Example 3

Flavored Sample 1.4 g of a tea flavoring was added to the sugar solution of Example 1, and thin layer sugar-coated tablets were obtained by the same coating method.

Comparative Example 1

Film Tablet

The uncoated tablets produced in the same manner as in Example 1 were coated by the Dria coater with a macromolecule solution prepared by stirring well 152 g of hydroxypropyl methyl cellulose 2910 (TC-5R), 39 g of hydroxypropyl methyl cellulose 2208 (SB-4), 50 g of talc, and 1.8 L of purified water to give a film coating of about 15 mg per tablet, thus giving film tablets.

Comparative Example 2

Sugar-Containing Film Tablet

The uncoated tablets produced in the same manner as in Example 1 were coated by the Dria coater with a macromolecule solution prepared by stirring well 152 g of sugar, 152 g of hydroxypropyl methyl cellulose 2910 (TC-5R), and 1.8 L of purified water to give a film coating of about 45 mg per tablet, thus giving film tablets.

Comparative Example 3

Two Layer Sugar-Coated Tablet

The uncoated tablets produced in the same manner as in Example 1 were coated by the Dria coater with a macromolecule solution prepared by stirring well 152 g of sugar, 152 g of hydroxypropyl methyl cellulose 2910 (TC-5R), and 1.8 L of purified water to give a film coating of about 20 mg per tablet as a protective layer.

Subsequently, 20 cycles of coating were carried out with a sugar syrup of 240 g of sugar and 0.13 L of purified water using a sugar coating pan, thus giving sugar-coated tablets of about 65 mg (syrup layer, about 45 mg) per tablet.

Comparative Example 4

Three Layer Sugar-Coated Tablet

Uncoated tablets produced in the same manner as in Example 1 were coated by the Dria coater with a macromolecule solution prepared by stirring well 152 g of hydroxypropyl methyl cellulose 2910 (TC-5R), 39 g of hydroxypropyl methyl cellulose 2208(SB-4), 50 g of talc, and 1.8 L of purified water to give a film coating of about 15 mg per tablet as a protective layer.

Subsequently, they were coated by the Dria coater with a macromolecule solution prepared by stirring well 152 g of sugar, 152 g of hydroxypropyl methyl cellulose 2910 (TC-5R), and 1.8 L of purified water to give a middle layer of about 46 mg per tablet.

Finally, 15 cycles of coating were carried out with a sugar syrup of 240 g of sugar and 0.13 L of purified water using a sugar coating pan, thus giving sugar-coated tablets with three coating layers of about 85 mg (syrup layer, about 24 mg) per tablet.

Comparative Example 5

Flavored Sample 2 g of a tea flavoring was added to the film solution of Comparative Example 2, and film tablets for comparison were produced by the same coating method.

Test Example 1

Sensory tests were carried out by six skilled panelists for the tablets obtained in Example 1 and Comparative Examples 1 and 2 in terms of slimy feel, sweetness, and preference. The results are shown in Table 1. The presence or absence of slimy feel was judged from whether or not there was a slimy feel when the tablet was put into the mouth, the presence or absence of sweetness was judged from whether or not there was sweetness when the tablet was put into the mouth, and preference was judged from whether or not the tablet was liked overall, respectively.

TABLE 1

|  | Slimy feel | Sweetness | Preference |
| --- | --- | --- | --- |
| Example 1 | ++ | + | ++ |
| Comparative Example 1 | − | −− | − |
| Comparative Example 2 | − | − | ± |

Slimy feel: ++ to −−, weak to strong
Sweetness: ++ to −−, strong to weak
Preference: ++ to −−, prefer to dislike It was confirmed from Table 1 that the sugar-coated preparation of Example 1 had better ease of taking than the film tablets of Comparative Examples 1 and 2.

Test Example 2

10 sugar-coated tablets obtained in Examples and Comparative Examples were dropped one by one from a height of 100 cm onto a glass surface, and the number of sugar-coated tablets that had cracked or peeled was counted. The results are given in Table 2.

Figure 2:
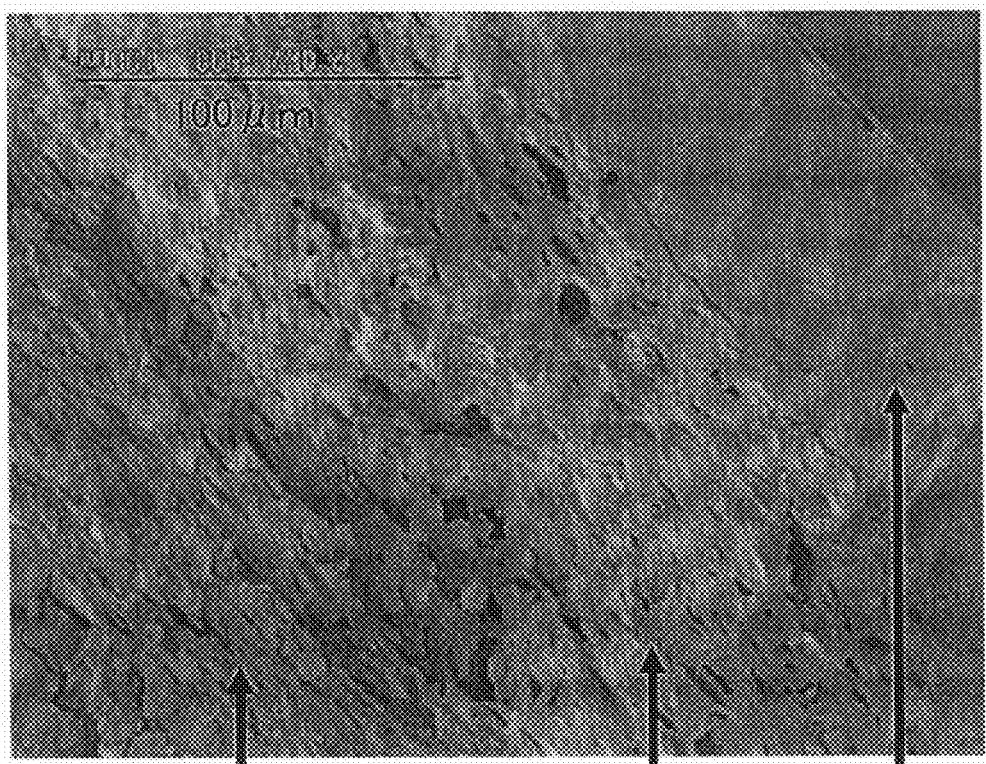

The tablets of Example 1 and Comparative Example 4 were sectioned using a cutter, and the cross sections were examined using a scanning electron microscope (SEM). FIG. 1 and FIG. 2 are diagrams showing SEM images of the cross sections of the sugar-coated tablets of Example 1 and Comparative Example 4 respectively.

TABLE 2

|  | No change | Cracking | Peeling |
| --- | --- | --- | --- |
| Example 1 | 10 | 0 | 0 |
| Example 2 | 10 | 0 | 0 |
| Comparative Example 3 | 2 | 6 | 2 |
| Comparative Example 4 | 0 | 8 | 2 |

As is clear from Table 2, it was found that the thin layer sugar-coated tablets of Examples 1 and 2 had high sugar coating strength compared with the sugar-coated tablets of Comparative Examples 3 and 4.

Furthermore, from FIG. 1 and FIG. 2 it was found that in the tablet of Example 1, no interface was formed in the coated layer, and in the tablet of Comparative Example 4 an interface was formed.

Test Example 3

After the tablets obtained in Example 3 and Comparative Example 5 had been stored at 65° C. for 2 weeks, a sensory test was carried out by five skilled panelists. It was found that in the tablet of Example 3 there was no change for the flavoring component, but in the film tablet of Comparative Example 5 the flavoring component could not be detected.

As is clear from the above, it was confirmed that when a flavoring was added to the thin layer sugar-coated tablet of Example 3, the flavoring component was stable.

Examples 4 to 17, Comparative Examples 6 to 16

Tablets were produced by using various types of sugar. Formulations of Examples and Comparative Examples are shown in Table 3-1 to Table 3-3, Table 4 to Table 7, Table 8-1, Table 8-2, and Table 9. In these Tables, the 'protective layer' corresponds to the 'film layer' in the above-mentioned embodiments, and the 'finishing layer' corresponds to the 'sugar coating layer' in the above-mentioned embodiments.

Table 3-1 and Table 3-2 relate to Examples and Comparative Examples in which the gradient layer and the middle layer were formed using a sugar or a sugar alcohol respectively.

Table 3-3 shows the formulation of the 'macromolecule solution' in Table 3-1, Table 3-2, Table 4, Table 6, and Table 8-1.

Table 4 relates to an Example in which a binder was added to the sugar solution.

Table 5 relates to Examples in which the gradient layer contained a plurality of hydroxypropyl celluloses.

Table 6 relates to Examples employing different methods for forming the finishing layer.

Table 7 relates to an Example and Comparative Examples which are different in terms of the presence or absence of a middle layer or the number of middle layers.

Table 8-1 and Table 8-2 relate to an Example and a Comparative Example in which a flavoring was added to the coated layer.

Table 9 relates to film tablets of Comparative Examples.

The procedure for the production of tablets of the Examples and Comparative Examples is described below.

[Uncoated Tablet]

Per tablet, 94.25 mg of lactose for direct tableting, 25 mg of crystalline cellulose, 10 mg of low-substituted hydroxypropyl cellulose, 0.75 mg of magnesium stearate, 15 mg of L-methionine, and 5 mg of vitamin B1-nitrate were mixed and compression-molded using a rotary tableting machine (CORRECT 12, manufactured by Kikusui Mfg. Co.). The tablets thus obtained had a tablet diameter of 7 mm, a 2 step R face shape, a hardness of about 4 kgf, and a weight per tablet of 150 mg.

[Coating]

The thin layer sugar-coated tablets in the Examples are formed from (1) a protective layer (film layer), (2) a gradient layer or a middle layer, and (3) a finishing layer (sugar coating layer).

In Examples 4 to 15, and 17, formation of the gradient layer was carried out by feeding the sugar solution and the macromolecule solution using two pumps and coating while changing the mixing ratio from the macromolecule base to the sugar base.

Furthermore, in Example 16, which has multiple middle layers, and Comparative Examples 6 to 12, which have one middle layer, the middle layer was formed by coating a mixture of the sugar solution and the macromolecule solution.

Control of spraying when forming the gradient layer and the middle layer was carried out by a twin pump system using the same apparatus as in Example 1 by the same continuous spray method as in the film tablet production method.

When coating with the finishing layer, the continuous spray method was mainly used. Furthermore, in Examples 6 and 9 and Comparative Examples 8 and 12, the finishing process was carried out by an intermittent liquid injection method. The intermittent liquid injection method is a normal method for producing a sugar-coated tablet, in which coating is carried out by kneading with a sugar syrup. As a coating apparatus, the continuous spray method employed a Dria coater (DRC-300, manufactured by Powrex Corp.), and the intermittent liquid injection method employed a sugar coating pan (manufactured by Kikusui Mfg. Co.). Good coating could be carried out by these coating methods.

With regard to the thin layer sugar-coated tablet, 700 g of uncoated tablets (inner core tablets) were coated with a spray solution of the formulation of each of the Examples and Comparative Examples by a spray method so that, per 150 mg of the inner core tablet, (1) the protective layer was 10 mg, (2) the gradient layer or the middle layer was 15 mg, and (3) the finishing layer was 10 mg, thus giving thin layer sugar-coated tablets in which the sugar coating layer weight was 23.3% (35 mg) relative to the inner core tablet (150 mg).

The coating conditions for the continuous spray method were: inlet air temperature 80° C., inlet air rate 0.5 m³/min, outlet air temperature 40° C. to 45° C., sprayfeed rate 4 g/min, and spray air pressure 0.15 MPa. Furthermore, in the intermittent liquid injection method, the liquid injected per cycle was 2 to 8 g, the gas supply temperature was 25° C. to 40° C., the process time per cycle was 10 min., and 10 to 15 cycles were carried out.

Furthermore, when forming the film layers of the film tablets of Comparative Examples 14 to 16, a liquid of the formulation shown in Table 8-2 and Table 9 was used for coating by the continuous spray method at 10 mg (Comparative Example 15) and 30 mg (Comparative Examples 14 and 16).

TABLE 3-1

| | | | Example 4 | Example 5 | Example 6 | Example 7 | Example 8 | Example 9 | Example 10 |
|---|---|---|---|---|---|---|---|---|---|
| Protective layer | | Macromolecule solution | 100 | 100 | 100 | 100 | 100 | 100 | 100 |
| Gradient layer | Macromolecule | Macromolecule solution | 53.5 | 53.5 | 53.5 | 53.5 | 53.5 | 53.5 | 53.5 |
| | Sugar | Sugar | 9.65 | | | | | | |
| | | Erythritol | | 9.65 | | | | | |
| | | Maltitol | | | 9.65 | | | | |
| | | Mannitol | | | | 9.65 | | | |
| | | Xylitol | | | | | 9.65 | | |
| | | Trehalose | | | | | | 9.65 | |
| | | Palatinit | | | | | | | 9.65 |
| | | Water | 43.85 | 43.85 | 43.85 | 43.85 | 43.85 | 43.85 | 43.85 |

TABLE 3-1-continued

|  |  | Example 4 | Example 5 | Example 6 | Example 7 | Example 8 | Example 9 | Example 10 |
|---|---|---|---|---|---|---|---|---|
| Finishing layer | Sugar | 10 | | | | | | |
| | Erythritol | | 10 | | | | | |
| | Maltitol | | | 10 | | | | |
| | Mannitol | | | | 10 | | | |
| | Xylitol | | | | | 10 | | |
| | Trehalose | | | | | | 10 | |
| | Palatinit | | | | | | | 10 |
| | Water | 45.4 | 454 | 45.4 | 45.4 | 45.4 | 45.4 | 45.4 |

TABLE 3-2

|  |  |  | Comparative Example 6 | Comparative Example 7 | Comparative Example 8 | Comparative Example 9 | Comparative Example 10 | Comparative Example 11 | Comparative Example 12 |
|---|---|---|---|---|---|---|---|---|---|
| Protective layer | | Macromolecule solution | 100 | 100 | 100 | 100 | 100 | 100 | 100 |
| Middle layer | Macromolecule | HPMC TC-5R | 3.21 | 3.21 | 3.21 | 3.21 | 3.21 | 3.21 | 3.21 |
| | | HPMC SB-4 | 1.07 | 1.07 | 1.07 | 1.07 | 1.07 | 1.07 | 1.07 |
| | | Talc JA-13R | 1.07 | 1.07 | 1.07 | 1.07 | 1.07 | 1.07 | 1.07 |
| | Sugar | Sugar | 9.65 | | | | | | |
| | | Erythritol | | 9.65 | | | | | |
| | | Maltitol | | | 9.65 | | | | |
| | | Mannitol | | | | 9.65 | | | |
| | | Xylitol | | | | | 9.65 | | |
| | | Trehalose | | | | | | 9.65 | |
| | | Palatinit | | | | | | | 9.65 |
| | | Water | 68.3 | 68.3 | 68.3 | 68.3 | 68.3 | 68.3 | 68.3 |
| Finishing layer | | Sugar | 10 | | | | | | |
| | | Erythritol | | 10 | | | | | |
| | | Maltitol | | | 10 | | | | |
| | | Mannitol | | | | 10 | | | |
| | | Xylitol | | | | | 10 | | |
| | | Trehalose | | | | | | 10 | |
| | | Palatinit | | | | | | | 10 |
| | | Water | 45.4 | 45.4 | 45.4 | 45.4 | 45.4 | 45.4 | 45.4 |

TABLE 3-3

| Macromolecule solution | |
|---|---|
| HPMC TC-5R | 9 |
| HPMC SB-4 | 3 |
| Talc JA-13R | 3 |
| Water | 135 |
| Total | 150 |

TABLE 5

| TC-5R:SB-4 mixing ratio | | | | |
|---|---|---|---|---|
| | | Example 4 | Example 13 | Example 14 |
| Protective layer | HPMC TC-5R | 6 | 4 | 2 |
| | HPMC SB-4 | 2 | 4 | 6 |
| | Talc JA-13R | 2 | 2 | 2 |
| | Water | 90 | 90 | 90 |

TABLE 4

| Sugar solution with binder added | | | | | |
|---|---|---|---|---|---|
| | | | Example 4 | Example 11 | Example 12 |
| Protective layer | | Macromolecule solution | 100 | 100 | 100 |
| Gradient layer | Macromolecule | Macromolecule solution | 53.5 | 53.5 | 53.5 |
| | Sugar | Sugar | 9.65 | 9.65 | 9.65 |
| | | HPMC SB-4 | | 0.4825 | |
| | | Gum arabic | | | 0.4825 |
| | | Water | 43.85 | 43.85 | 43.85 |
| Finishing layer | | Sugar (Continuous spray method) | 10 | 10 | 10 |
| | | HPMC SB-4 | | 0.5 | |
| | | Gum arabic | | | 0.5 |
| | | Water | 45.4 | 45.4 | 45.4 |

TABLE 5-continued

TC-5R:SB-4 mixing ratio

|  |  |  | Example 4 | Example 13 | Example 14 |
|---|---|---|---|---|---|
| Gradient layer | Macromolecule | HPMC TC-5R | 3.21 | 2.14 | 1.07 |
|  |  | HPMC SB-4 | 1.07 | 2.14 | 3.21 |
|  |  | Talc JA-13R | 1.07 | 1.07 | 1.07 |
|  |  | Water | 48.15 | 48.15 | 48.15 |
|  | Sugar | Sugar | 9.65 | 9.65 | 9.65 |
|  |  | Water | 68.3 | 68.3 | 68.3 |
| Finishing layer |  | Sugar | 10 | 10 | 10 |
|  |  | Water | 45.4 | 45.4 | 45.4 |

TABLE 6

Examination of imparting barrier properties

|  |  |  | Example 4 | Example 15 |
|---|---|---|---|---|
| Protective layer |  | Macromolecule solution | 100 | 100 |
| Gradient layer | Macromolecule | Macromolecule solution | 53.5 | 53.5 |
|  | Sugar | Sugar | 9.65 | 9.65 |
|  |  | Water | 43.85 | 43.85 |
| Finishing layer |  | Sugar (Continuous spray method) | 10 |  |
|  |  | Sugar (Intermittent liquid injection method) |  | 10 |
|  |  | Water | 45.4 | 4.29 |

TABLE 7

Multistep

|  |  | Example 16 | Comparative Example 6 | Comparative Example 13 |
|---|---|---|---|---|
| Protective layer | HPMC TC-5R | 6 | 6 | 10.5 |
|  | HPMC SB-4 | 2 | 2 | 3.5 |
|  | Talc JA-13R | 2 | 2 | 3.5 |
|  | Water | 90 | 90 | 157.5 |
| Middle layer | HPMC TC-5R | 2.04 | 3.21 |  |
|  | HPMC SB-4 | 0.68 | 1.07 |  |
|  | Talc JA-13R | 0.68 | 1.07 |  |
|  | Sugar | 4.1 | 9.65 |  |
|  | Water | 49.3 | 68.3 |  |
|  | HPMC TC-5R | 0.54 |  |  |
|  | HPMC SB-4 | 0.18 |  |  |
|  | Talc JA-13R | 0.18 |  |  |
|  | Sugar | 6.6 |  |  |
|  | Water | 38.2 |  |  |
| Finishing layer | Sugar | 10 | 10 | 17.5 |
|  | Water | 4.29 | 4.29 | 7.5 |

TABLE 8-1

Examination of addition of flavoring

|  |  | Example 17 |
|---|---|---|
| Protective layer | Macromolecule solution | 100 |
| Gradient layer | Macromolecule Macromolecule solution | 53.5 |
|  | Sugar Sugar | 9.65 |
|  | Tea flavoring | 0.017 |
|  | Water | 43.85 |

TABLE 8-1-continued

Examination of addition of flavoring

|  |  | Example 17 |
|---|---|---|
| Finishing layer | Sugar (intermittent liquid injection method) | 10 |
|  | Tea flavoring | 0.018 |
|  | Water | 4.29 |

TABLE 8-2

Flavored film tablet

|  |  | Comparative Example 14 |
|---|---|---|
| Film layer | HPMC TC-5R | 15 |
|  | Sugar | 15 |
|  | Tea flavoring | 0.017 |
|  | Water | 170 |

TABLE 9

Film tablet

|  |  | Comparative Example 15 | Comparative Example 16 |
|---|---|---|---|
| Film layer | HPMC TC-5R | 6 | 15 |
|  | HPMC SB-4 | 2 |  |
|  | Talc JA-13R | 2 |  |
|  | Sugar |  | 15 |
|  | Water | 90 | 170 |

Test Example 4

A drop test, an odor evaluation test, an examination of the permeation of moisture, a flavoring stability test, and an ease of taking test were carried out. The method for each test is explained below.

[Drop Test]

10 tablets of Examples 4 to 16 and Comparative Examples 6 to 13 were dropped one by one from a height of 100 cm onto a glass surface. The number of drops was 3, and the occurrence of peeling and cracking was examined. Evaluation was made in accordance with the criteria below, with 0 to 40 evaluation points.

4: Peeling at first drop.

3: Peeling at second drop.

2: Peeling at third drop.

1: Fine cracking at third drop.

0: No change.

Peeling was judged from whether or not part of the sugar coating layer was chipped immediately after dropping. When evaluating, 10 or less points was good, 11 or more and 15 or less points was fair, and 16 or more points was poor.

[Odor Evaluation Test (GC/MS Method)]

40 tablets of Examples 4 and 15 and Comparative Example 15 were stored at 65° C. for 2 weeks, and a quantitative analysis of the odor of methanethiol, which is a decomposition product of L-methionine, was carried out by gas chromatography (GC/MS method).

[Odor Evaluation Test (Sensory Evaluation)]

50 tablets of Examples 4 and 15 and Comparative Example 15 were stored at 40° C. for 2 weeks, and a sensory evaluation was then carried out by eight skilled panelists.

The number of evaluation points was based on the criteria below, and when the average was less than 2 it was evaluated as being good.

4: Marked change in odor was sensed.
3: Change in odor was sensed.
2: Change in odor was sensed but it was acceptable.
1: Slight change in odor was sensed.
0: No change.

[Examination of Permeation of Moisture (Stability Test)]

50 tablets of Examples 4 and 15 and Comparative Example 15 were stored in an open bottle at 40° C. and 75% RH for 2 weeks, then stored in a closed bottle at 65° C. for 1 week, and the amount of vitamin B1 remaining in the sample was quantitatively measured by high performance liquid chromatography (Waters).

[Examination of Permeation of Moisture (Moisture Absorption Test)]

50 tablets of Examples 4 and 15 and Comparative Example 15 were stored in an open bottle at 25° C. and 60% RH for 2 weeks, 6 tablets were ground, and an equilibrium relative humidity (ERH, %) was measured.

[Flavoring Stability Examination (Sensory Test)]

50 tablets of Example 17 and Comparative Example 14 were stored at 65° C. for 2 weeks, and a sensory test was then carried out by eight skilled panelists. Evaluation was made on the basis of a change in the flavoring component.

[Ease of Taking Test (Sensory Test)]

A sensory test for the tablets of Example 4 and Comparative Examples 15 and 16 was carried out by skilled panelists. Evaluation was made with 5 points as a full mark in terms of 'appearance' 'ease of taking', and 'taste'.

Next, the results of each of the above-mentioned tests are given.

[Drop Test]

Table 10 shows the results of the drop test.

Moreover, in Example 15 also, in which the intermittent liquid injection method was carried out for the finishing process in order to achieve barrier properties, sufficient strength could be obtained in the same manner as for a case in which the continuous spray method was used.

Furthermore, in Example 16 also, in which a two step middle layer was provided, sufficient strength could be obtained. It was found from this that even by coating stepwise simply using a single pump, a thin layer sugar-coated tablet having excellent strength could be produced.

On the other hand, in Comparative Example 6, in which a middle layer having a uniform sugar concentration was provided, and in Comparative Example 13, in which no middle layer was provided, the evaluation results for strength were 'poor'.

[Odor Evaluation Test (GC/MS Method)]

Figure 3:
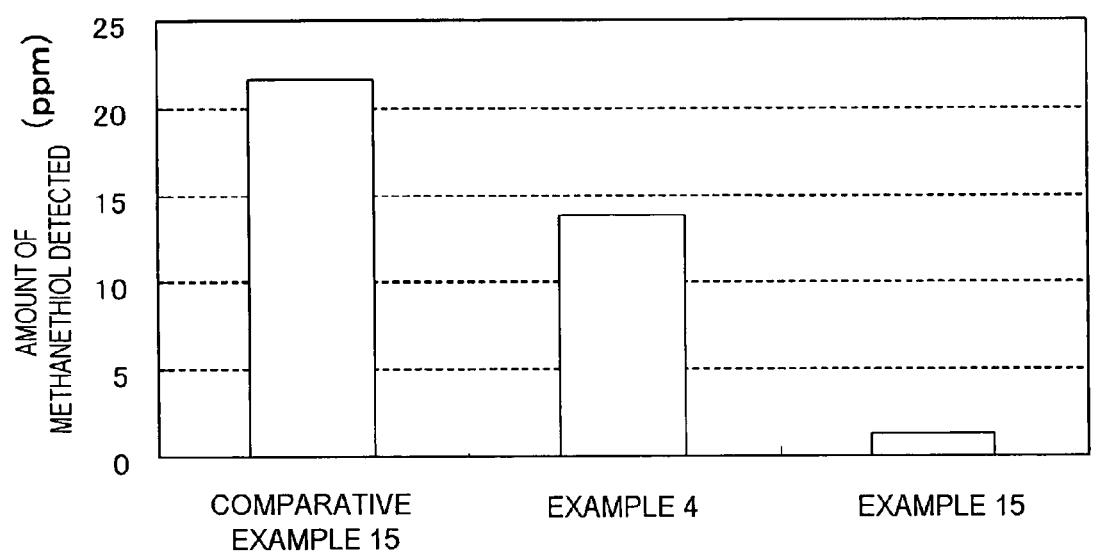

The evaluation results by the GC/MS method are shown in FIG. 3. It was found from FIG. 3 that in Example 4, by coating by the continuous spray method with the sugar solution for the finishing layer (sugar coating layer), compared with Comparative Example 15, which was for the film tablet, permeation of methanethiol, which is a decomposition product of L-methionine, could be suppressed to some extent. Furthermore, in Example 15, in which coating was carried out by the intermittent liquid injection method, permeation of methanethiol could be suppressed completely.

[Odor Evaluation Test (Sensory Evaluation)]

Figure 4:
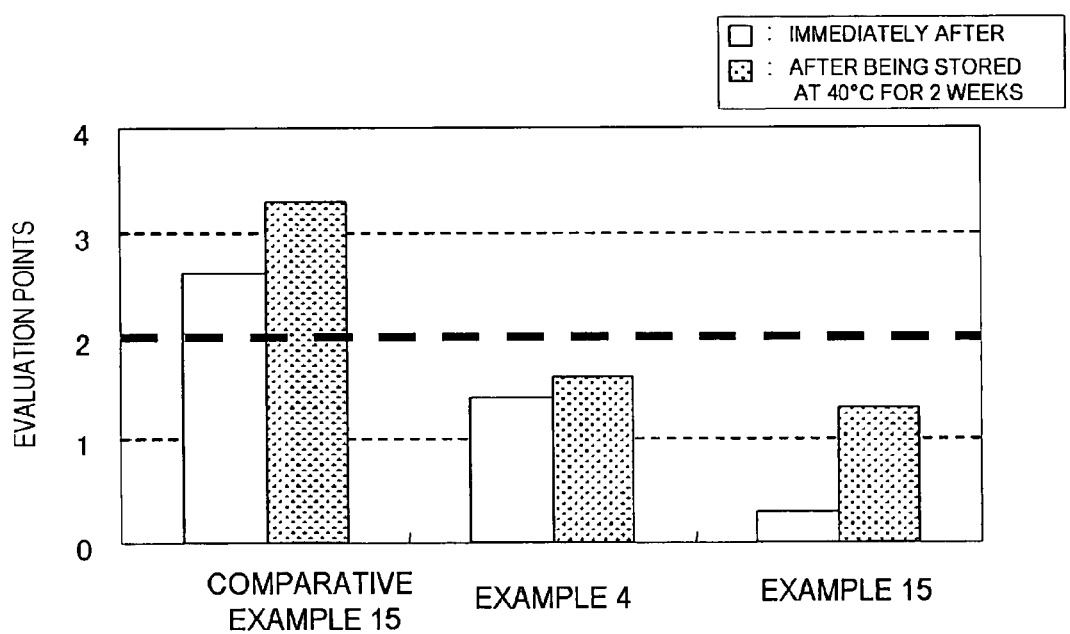

The results of the sensory evaluation are shown in FIG. 4. From FIG. 4, in the sugar-coated tablets of Examples 4 and 15, good results could be obtained. Furthermore, it can be said from the results of FIG. 4 and the above-mentioned results by the GC/MS method that the thin layer sugar-coated tablets of the Examples have barrier properties with respect to the permeation of odor.

[Examination of Permeation of Moisture (Stability Test)]

Figure 5:
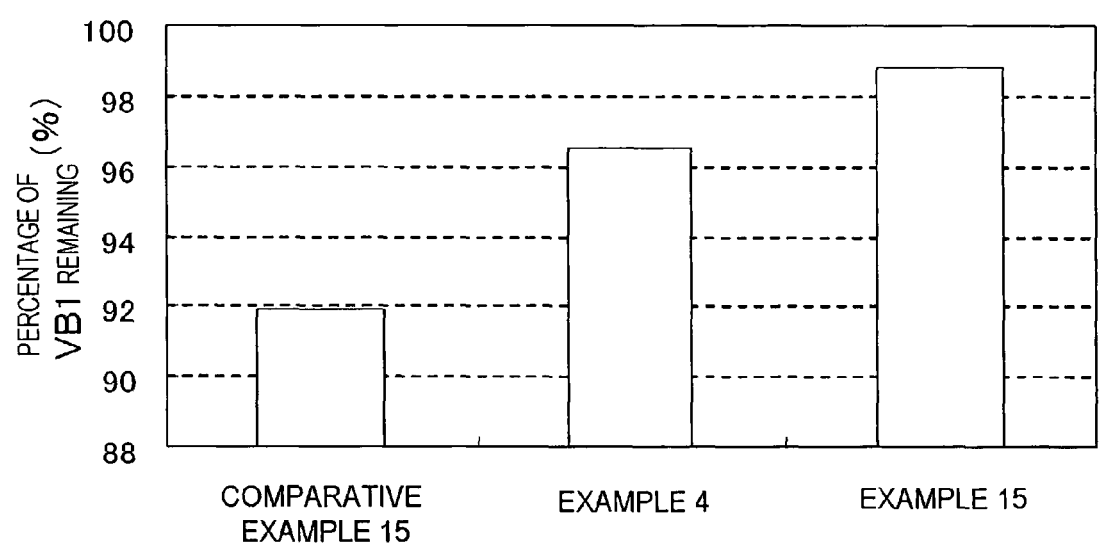

FIG. 5 is a diagram showing the results of a vitamin B1 (VB1) stability test when storing in an open bottle at 40° C. and 75% RH for 2 weeks and then storing at 65° C. for 1 week. From FIG. 5, by coating by the continuous spray method with

TABLE 10

| | Example 4 | Example 5 | Example 6 | Example 7 | Example 8 | Example 9 | Example 10 | Example 11 | Example 12 | Example 13 | Example 14 | Example 15 | Example 16 |
|---|---|---|---|---|---|---|---|---|---|---|---|---|---|
| Points | 6 | 6 | 8 | 1 | 6 | 3 | 5 | 3 | 8 | 10 | 13 | 5 | 8 |
| Evaluation | Good | Good | Good | Good | Good | Good | Good | Good | Good | Good | Fair | Good | Good |

| | Comparative Example 6 | Comparative Example 7 | Comparative Example 8 | Comparative Example 9 | Comparative Example 10 | Comparative Example 11 | Comparative Example 12 | Comparative Example 13 |
|---|---|---|---|---|---|---|---|---|
| Points | 20 | 21 | 13 | 4 | 16 | 32 | 11 | 21 |
| Evaluation | Poor | Poor | Fair | Good | Poor | Poor | Fair | Poor |

In Table 10, from the results of Examples 4 to 10 and the results of Comparative Examples 6 to 12, for any of the sugars and the sugar alcohol, by forming the coated layer without an interface by coating with the gradient layer, a sugar-coated tablet having high drop resistance could be obtained when compared with the thin layer sugar-coated tablet formed from three layers using the same sugar.

Furthermore, as in Examples 11 and 12, by adding a binder to the sugar solution, a thin layer sugar-coated tablet having sufficient strength could be formed.

From Examples 4, 13, and 14, in which the mixing ratio of TC-5R and SB-4 in the macromolecule solution was changed, by employing the mixing ratio TC-5R:SB-4=3:1, the strength could be further improved.

the sugar solution for the finishing layer in Example 4, it was possible to suppress moisture to some extent, which influenced the stability of vitamin B1, and improve the stability compared with Comparative Example 15, which was a film tablet. Moreover, in Example 15 in which coating for the finishing layer was carried out by the intermittent liquid injection method, moisture could be substantially completely suppressed, and hardly any degradation in the stability was observed.

[Examination of Permeation of Moisture (Moisture Absorption Test)]

Figure 6:
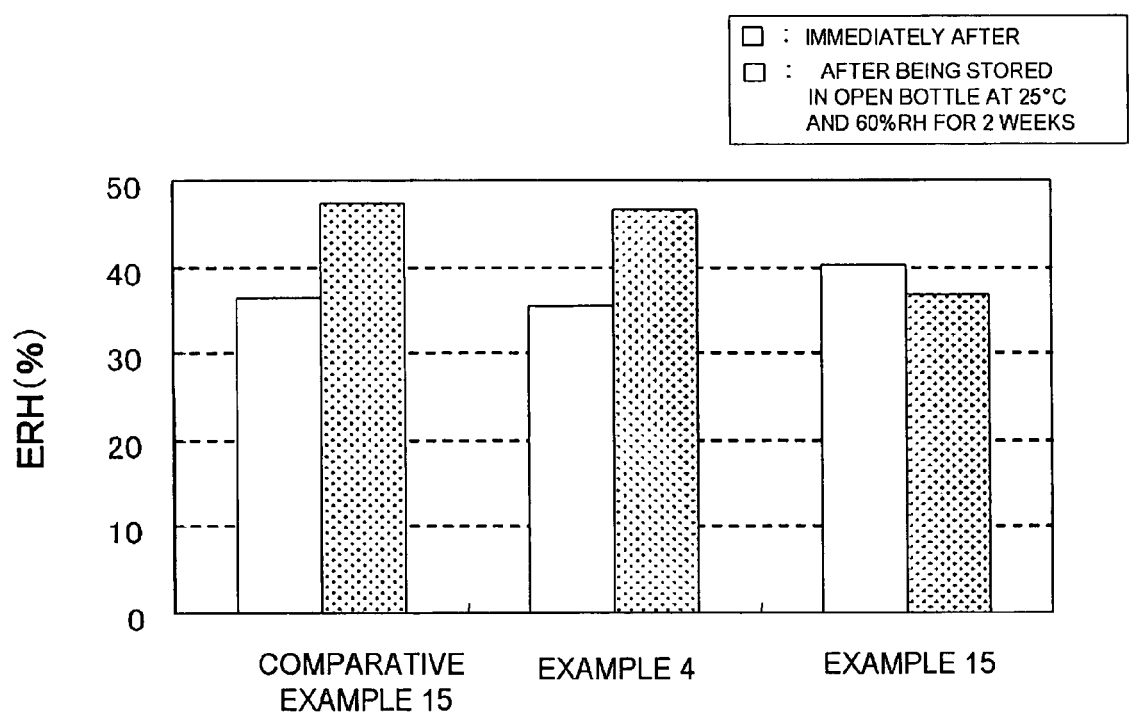

FIG. 6 is a diagram showing the results of a moisture absorption test of a product stored in an open bottle at 25° C. and 60% RH for 2 weeks. In FIG. 6, the ordinate denotes equilibrium relative humidity (ERH (%)). It can be said from the results of FIG. 6 and the above-mentioned results of the vitamin B1 stability test that the thin layer sugar-coated tablets obtained in Examples 4 and 15 had barrier properties with respect to the permeation of moisture. In particular, it was found that in Example 15, in which coating of the finishing layer was carried out by the intermittent liquid injection method, the barrier properties were further improved, and permeation of moisture during storage could be substantially completely prevented.

[Examination of Flavoring Stability (Sensory Test)]

Table 11 shows the results of a sensory test related to a flavoring. It was found from Table 11 that the thin layer sugar-coated tablet in Example 17 had an effect in stabilizing the flavoring in the sugar coating layer.

TABLE 11

|  | No Change | Change |
|---|---|---|
| Example 17 | 8 | 0 |
| Comparative Example 14 | 2 | 6 |

[Ease of Taking Test (Sensory Test)]

Figure 7:
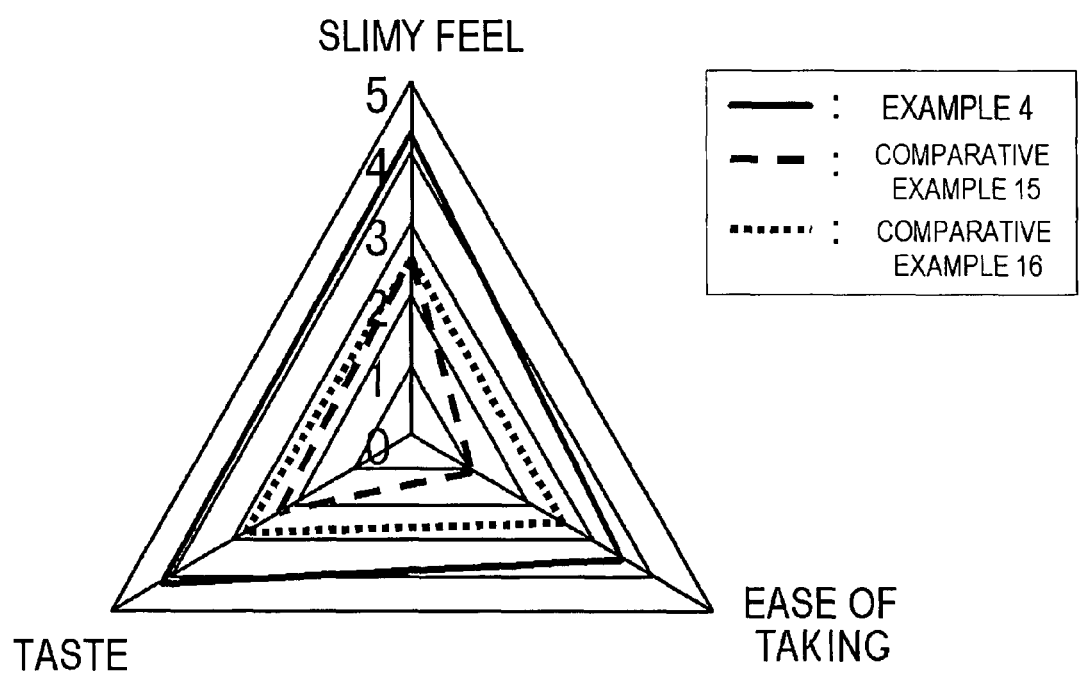

FIG. 7 is a diagram showing the results of a sensory test for ease of taking. It was found from FIG. 7 that the thin layer sugar-coated tablet of Example 4 had excellent ease of taking compared with the film tablets of Comparative Examples 15 and 16.

From the above Examples, a thin layer sugar-coated tablet having a sugar coating layer at 50% or less of the weight of the inner core tablet could be obtained, the thin layer sugar-coated tablet having characteristics such as an 'attractive surface', 'excellent ease of taking', 'high strength', 'ability to mask an odor', or 'barrier properties with respect to moisture'.

In the above Examples, as a constitution in which the sugar coating component concentration in the middle layer changes stepwise, two middle layers having different sugar coating component concentrations were formed, but three or more middle layers may be formed.

The invention claimed is:

1. A sugar-coated agent comprising:
A core;
a film layer mainly comprising a film component, the outer surface of said core being coated with the film layer;
a sugar coating layer mainly comprising a sugar coating component, the outside of said film layer being coated with the sugar coating layer; and
a middle layer comprising a film component and a sugar coating component, the middle layer being provided between said film layer and said sugar coating layer;
within said middle layer, the concentration of said sugar coating component at the interface between said middle layer and said sugar coating layer being higher than the concentration of said sugar coating component at the interface between said middle layer and said film layer, and wherein said middle layer comprises a gradient layer, the concentration of said sugar coating component in said gradient layer continuously increasing steplessly from the film layer side to the sugar coating layer side.

2. The sugar-coated agent according to claim 1, wherein said middle layer is formed from one or more of said gradient layers.

3. The sugar-coated agent according to claim 1, wherein, in going from said film layer to said sugar coating layer, the sugar-coated agent has no discontinuous plane at which the composition of said sugar coating component changes discontinuously.

4. The sugar-coated agent according to claim 1, wherein said film component is one or more materials selected from the group consisting of hydroxypropyl methyl cellulose, gum arabic, polyvinyl pyrrolidone, polyvinyl alcohol, and pullulan.

5. The sugar-coated agent according to claim 1, wherein said film component is a mixture of hydroxypropyl methyl cellulose 2910 and hydroxypropyl methyl cellulose 2208.

6. The sugar-coated agent according to claim 1, wherein said sugar coating component is one or more selected from the group consisting of sucrose, erythritol, mannitol, sorbitol, xylitol, maltitol, and reduced lactose.

7. The sugar-coated agent according to claim 1, wherein said sugar-coated agent is a sugar-coated tablet.

8. The sugar-coated agent according to claim 1, wherein said middle layer further comprises a flavoring.

9. A process for producing the sugar-coated agent according to claim 1, the process comprising:
coating the outer surface of the core with said film layer,
coating the outside of the film layer with the sugar coating layer,
providing the middle layer between the film layer and the sugar coating layer,
wherein said middle layer is formed by spraying a mixed liquid of a first liquid containing a film component and a second liquid containing a sugar coating component onto said core while continuously changing the mixing ratio of said first liquid and said second liquid in said mixed liquid to form said gradient layer by continuously increasing steplessly the concentration of the second liquid containing the sugar coating component from the film layer side to the sugar coating layer side.

10. A process for producing the sugar-coated agent according to claim 9, the process comprising:
wherein said middle layer is formed by a sprayer employing at least two liquid feed pumps, that is, a liquid feed pump that feeds the first liquid comprising a film component and a liquid feed pump that feeds the second liquid comprising a sugar coating component while continuously changing the flow rate of each of the liquid feed pumps.

11. The process according to claim 10, wherein each of the liquids are mixed partway along a pipe and supplied.

12. A sugar-coated agent wherein, with regard to a solid preparation comprising a core coated with a coated layer, said coated layer comprises as components a film component and a sugar coating component, said coated layer having a portion that is closest to the core coated with a coating agent comprising the film component alone or mainly comprising the film component, the proportion of the sugar coating component continuously increasing steplessly as it goes further from the core, and the outermost layer having a coated layer that is coated with a coating agent comprising the sugar coating component alone or mainly comprising the sugar coating component.

* * * * *